United States Patent
Lancaster et al.

(10) Patent No.: US 11,229,801 B2
(45) Date of Patent: Jan. 25, 2022

(54) SINGLE USE DETECTOR FOR AN AUTOMATED EXTERNAL DEFIBRILLATOR (AED)

(71) Applicant: KONINKLIJKE PHILIPS N.V., Eindhoven (NL)

(72) Inventors: Gregory James Lancaster, Seattle, WA (US); Dennis E. Ochs, Woodinville, WA (US)

(73) Assignee: Koninklijke Philips N.V., Eindhoven (NL)

( * ) Notice: Subject to any disclaimer, the term of this patent is extended or adjusted under 35 U.S.C. 154(b) by 205 days.

(21) Appl. No.: 16/341,087

(22) PCT Filed: Oct. 10, 2017

(86) PCT No.: PCT/EP2017/075722
§ 371 (c)(1),
(2) Date: Apr. 11, 2019

(87) PCT Pub. No.: WO2018/069264
PCT Pub. Date: Apr. 19, 2018

(65) Prior Publication Data
US 2019/0232068 A1  Aug. 1, 2019

Related U.S. Application Data

(60) Provisional application No. 62/407,572, filed on Oct. 13, 2016.

(51) Int. Cl.
*A61N 1/39*          (2006.01)
(52) U.S. Cl.
CPC ......... *A61N 1/3925* (2013.01); *A61N 1/3904* (2017.08); *A61N 1/3993* (2013.01)

(58) Field of Classification Search
CPC ........................... A61N 1/3925; A61N 1/3975
See application file for complete search history.

(56) References Cited

U.S. PATENT DOCUMENTS

| | | | | |
|---|---|---|---|---|
| 6,154,673 A | * | 11/2000 | Morgan | A61N 1/3904 607/5 |
| 2003/0055459 A1 | * | 3/2003 | Lyster | A61N 1/0492 607/5 |
| 2004/0143297 A1 | | 7/2004 | Ramsey, III | |
| 2005/0277991 A1 | * | 12/2005 | Covey | A61N 1/0492 607/5 |
| 2013/0317560 A1 | * | 11/2013 | Barnes | A61N 1/3993 607/6 |
| 2015/0046175 A1 | | 2/2015 | Jorgenson et al. | |

FOREIGN PATENT DOCUMENTS

WO    2006102420 A2    9/2006

OTHER PUBLICATIONS

PCTEP2017/075722 ISR and Written Opinion, dated Jan. 22, 2018.

\* cited by examiner

*Primary Examiner* — Alyssa M Alter

(57) ABSTRACT

Systems and methods of limiting activation of a single use automated external defibrillator (AED). The method comprises using an event monitoring module to sense an activation of the AED, monitor the AED's use state, generate a notification and request a deactivation command if the AED's use state satisfies at least one deactivation criterion, and deactivating the AED when a deactivation command is received. The AED device comprises an energy source, a pair of electrodes, an alert module, a wireless communication module, and an event monitoring module.

7 Claims, 6 Drawing Sheets

|  | AED use state |
|---|---|
| Total activation time | 28 minutes |
| Pads deployed events | 1 |
| Pads deployed NSA time | 5 minutes |
| Pads deployed shock advised events | 0 |

SINGLE USE DETECTOR FOR AN AUTOMATED EXTERNAL DEFIBRILLATOR (AED)

CROSS-REFERENCE TO PRIOR APPLICATIONS

This application is the U.S. National Phase application under 35 U.S.C. § 371 of International Application No. PCT/EP2017/075722, filed on Oct. 10, 2017, which claims the benefit of U.S. Provisional Patent Application No. 62/407,572, filed on Oct. 13, 2016. These applications are hereby incorporated by reference herein.

BACKGROUND OF THE INVENTION

Cardiac arrest, ventricular fibrillation and cardiac arrhythmia are life-threatening heart conditions that require immediate cardiopulmonary resuscitation (CPR) and defibrillation to increase one's chances of survival. Defibrillation is a treatment that involves the delivery of an electric shock that allows reestablishment of the normal contraction rhythms of the heart.

Over-the-counter and single use automated external defibrillators (AED) are commercially available for use in private residences and offer the advantage of providing immediate assistance during cardiac arrests at home. Single use AEDs are typically usable for a single rescue operation only and capable of delivering a limited number of shocks. Single use AEDs provide a low cost solution—since some of the AED components are disposable—to individuals who desire an AED unit at home but do not expect frequent cardiac arrests.

One of the challenges with home-installed AEDs is that the long latency between installation and use tends to make owners unfamiliar with the operation of the AED during a rescue operation. Although instructions are provided audibly via the speaker and graphically on the AED screen and the electrode pads, the unfamiliarity and the psychological pressure can make the user hesitate to use the AED. In other times, the necessity of using the AED may not be clear to the user, and the user may also hesitate to use the AED due to the expense of unnecessarily changing the electrode pads and battery afterwards.

U.S. Patent Application No. 2015/0046175 discloses a single use AED capable of recording event data during a rescue operation, performing self-tests to detect problems, generating alerts, and communicating with a docking station. U.S. Patent Application No. 2013/0317560 discloses an AED with a status detector for determining the status of an AED during operation. Alarms are generated when the status detector detects a not-ready-to-use state.

BRIEF SUMMARY OF THE INVENTION

The present invention relates to systems and methods for limiting an activation of an automated external defibrillator (AED). Such a limitation appears to be counter-intuitive, but the inventors have discovered that such limiting before the battery or the pads are completely used up provides significant benefits to the customer. For example, a single use device by its nature results in improved reliability because there is less opportunity for a fault to occur. The device, after such a single use, would be returned for service or serviced in place or replaced in its entirety for the next use. In addition, a single use device may enable a lower cost of ownership because the overhead for long-term quality control of the device is replaced by quick and inexpensive refurbishment and replacement with new devices. Finally, a single use device lessens the likelihood that a customer, in an attempt to extend the life of the device, would pull the battery and so disable all further self-testing.

When the AED is activated, an event monitoring module detects the AED activation and monitors the AED's use state. The event monitoring module then determines whether the AED's use state satisfies a deactivation criterion, such as a total activation time, the number of electrode pads deployed, the duration of a No Shock Advised event, and the generation of a shock. When at least one deactivation criterion has been satisfied, an alert is generated locally at the AED's user interface and/or from the AED's wireless communication module to a central monitoring server, prompting the user to deactivate the AED and replace the electrode pads and battery. Deactivation may be conducted by the user locally at the user interface or may be accomplished from a remote location via the wireless communication module. The AED also comprises an external electrode connector to enable easy replacement of the electrode pads. The AED wireless communication module may also be used to for establish communication with a central monitoring server during rescue operations and/or to communicate the need to maintain or repair the AED.

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings.

DETAILED DESCRIPTION OF THE VARIOUS EMBODIMENTS OF THE INVENTION

Figure 1:
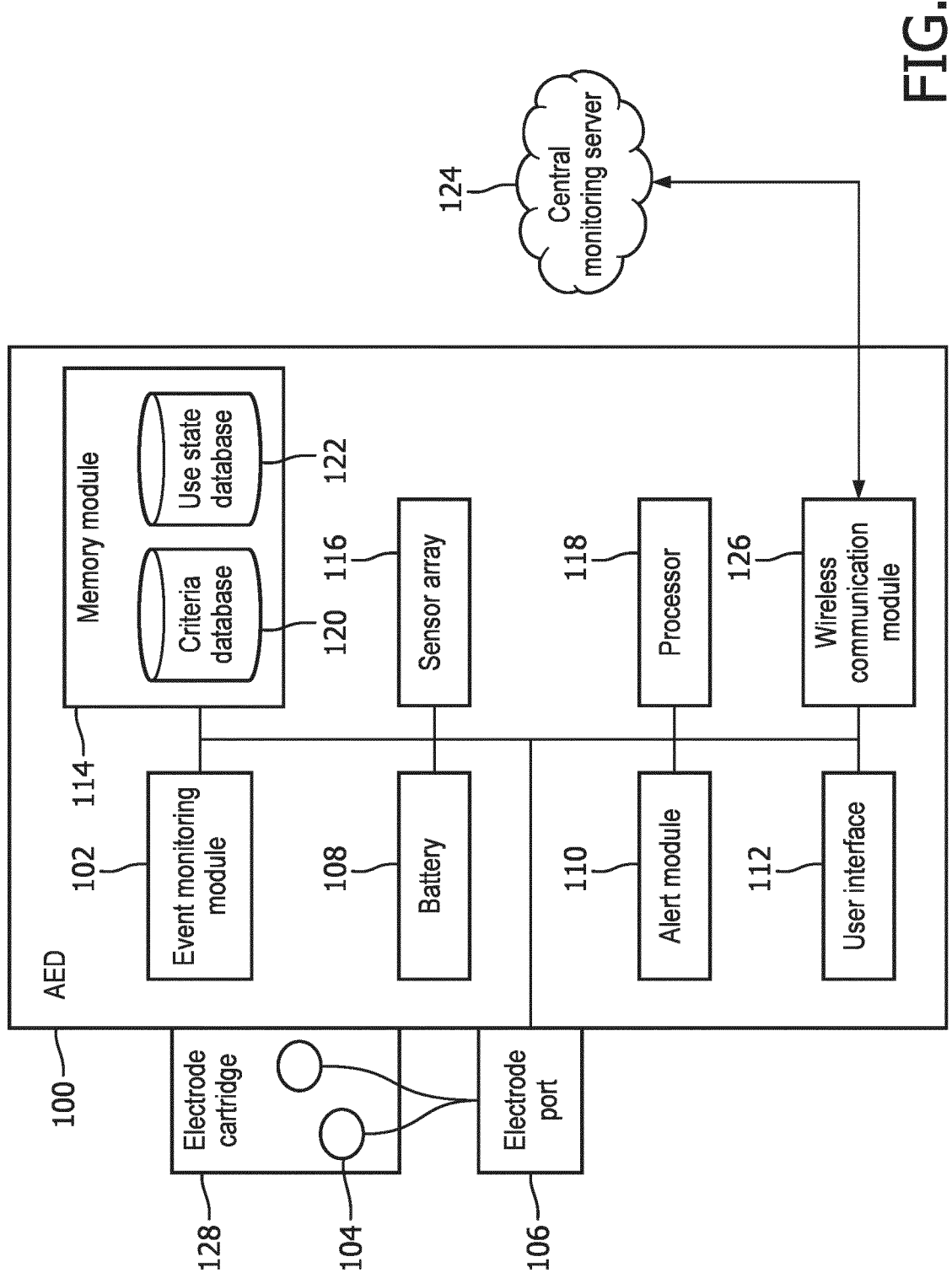
FIG. 1 is a block diagram of an AED device according to a preferred embodiment of the present invention.

The following are definitions of terms as used in the various embodiments of the present invention.

The term "single use AED" as used herein refers to an AED in which after a single use, the AED will require a maintenance service to replace one or more disposable components such as battery and electrode pads or require the replacement of the AED with a new unit.

The term "use state" as used herein refers to information relating to one or more AED features or functionalities, including activation, deactivation, switching ON, switching to standby mode, electrode pad deployment, "Shock Advised" event, and "No Shock Advised" (NSA) event, among others.

The term "event monitoring module" as used herein refers to one or more hardware and software for monitoring the AED's use state. The event monitoring module includes battery monitors, timers, environment sensors, and circuitry, among others, to enable the monitoring of the AED's use state.

The term "Ready for Use" as used herein refers to a state in which the AED is operable for use. The term "Not Ready for Use" as used herein refers to a state where the AED can no longer perform an intended functionality. This may arise due to a depleted battery, overused electrode pads, or a malfunctioning component, for example.

The term "deactivated state" refers to a state where the AED is prevented from being used or activated until a maintenance or service operation is performed. The term "standby state" as used herein refers to a low-power "Ready for Use" state. The term "active state" refers to a "Ready for Use" state commencing from the pressing of the ON button. The term "activation time" as used herein refers to a duration of one or more active states.

The term "deployment" as used herein refers to the removal of the electrode pads from the electrode cartridge on the AED and the mounting of the electrode pads on a body part.

The present invention relates to a method of limiting an activation of a single use AED using an event monitoring module comprising: sensing an activation of the AED; monitoring the AED's use state; generating a notification and requesting a deactivation command if the AED's use state satisfies at least one deactivation criterion; deactivating the AED when a deactivation command is received.

The present invention also relates to a single use AED device, comprising an energy source, a pair of electrodes, a wireless communication module for communicating with a central monitoring server, an event monitoring module for monitoring the AED's use state during an activation period, and an alert module for alerting the user of AED's use state.

In a preferred embodiment of the present invention, the single use AED comprises a pair of disposable electrodes and a low capacity battery that is capable of delivering a limited number of shocks during a single rescue operation. Preferably, voice prompts and graphical instructions on the electrode pads and on the AED display screen are also provided to guide a user who has limited training in using an AED. The electrode pads are mounted on the patient's upper right chest and lower left ribcage. The AED then analyzes the patient's heart rhythm to determine if there is a shockable heart rhythm (e.g., ventricular fibrillation, ventricular tachycardia and supraventricular tachycardia). If a shockable heart rhythm is detected, the AED generates a "Shock Advised" alert and prompts the user to press a shock button to deliver the shock. If no shockable heart rhythm is detected, the AED generates a "No Shock Advised" (NSA) alert.

During a rescue operation, the AED preferably dials an emergency hotline to request assistance for the emergency. Upon arrival of medical personnel, the AED is queried to determine the status of the rescue operation, and the rescue operation may be continued as needed. The disposable electrode pads and battery are then replaced by an AED technician.

FIG. 1 illustrates a schematic block diagram of an AED 100 according to a preferred embodiment of the present invention. As shown, the AED 100 comprises an event monitoring module 102, electrode pads 104, electrode port 106, battery 108, alert module 110, user interface 112, memory module 114, sensor array 116, processor 118, and electrode cartridge 128. The memory module 114 comprises a criteria database 120 and a use state database 122. The AED 100 is capable of connecting to a central monitoring server 124 via the wireless communication module 126.

The event monitoring module 102 preferably comprises a counting means, e.g. a computer-controlled digital counter, to monitor the number of times the AED 100 is activated, the number of times the electrode pads 104 are deployed, and the number of times a shock command is received from a user in response to a "Shock Advised" event. The event monitoring module 102 also preferably comprises a timing means, such as a digital clock circuit, to record the duration of each AED activity, such as an AED activation, a shock event, or an NSA event, among others. The event monitoring module 102 is preferably coupled to one or more input means (e.g. buttons, power switch) of the user interface 112 so that every new input signal is recorded by the event monitoring module 102. For example, when a power switch is pressed, the event monitoring module 102 senses an ON or activation event. The counting means increments the ON-count value by 1 every time the event monitoring module senses an ON event. The timing means records then ON event to the memory module 114 with a time stamp then starts a timer from a base value, preferably 0 second. When the power switch is pressed the second time, the counting means adds a value to the OFF-count value. But preferably, before the power to the AED is switched off after the power switch is pressed a second time, the timing means ends the timer and the activation time is determined to be the time indicated on the stopped timer. Preferably, the activation time is a cumulative value from all the activation times that have occurred since the last replacement of battery 108. When the battery 108 has been replaced, the activation time is preferably reset to 0. The event monitoring module 102 also preferably comprises a battery monitor to monitor and manage the power consumption of the AED 100. It is understood that "counting means" and "timing means" and "input means" comprise hardware and associated software instructions, such as hardware processors, clocks, computer controllers, and digital/analog signal streams respectively.

The electrode pads 104 are preferably disposable electrode pads that require replacement preferably after a single use or after the generation of a limited number of shocks. In some embodiments of the invention, the electrode pads 104 may be reused if no shocks have been generated. For example, the electrode pads 104 may be attached to the patient to attempt defibrillation during a cardiac arrest, but the processor 118 may determine an NSA event. The user may then reuse the electrode pads 104 if only a short time has elapsed during the NSA event. In a preferred embodiment, the electrode pads 104 are preferably removably coupled to the AED 100 via the electrode port 106 to allow easy replacement of the electrode pads 104. Preferably, the electrode port 106 is external to the AED housing. Alternatively, the electrode port 106 is located inside the AED housing and inaccessible to the user to minimize user involvement in setting up the AED 100 and to minimize the risk of accidentally detaching the electrode pads 104. Preferably, maintenance personnel perform the replacement of electrode pads 104.

In a preferred embodiment, the electrode pads 104 are stowed in the AED 100 via the electrode cartridge 128 that enables easy deployment and re-stowing of the electrode pads 104. The electrode cartridge 128 may comprise attachment means such as adhesives, Velcro, fasteners, hooks, and pockets, for example. When the electrode pads 104 are not used extensively during a rescue operation (e.g., an NSA event), the electrode pads 104 may be re-stowed in the electrode cartridge 128.

Preferably, the battery 108 is removably attached to the AED 100 via a simple attachment means such as a fastener, clip, and screw, among others, so the AED owner can easily replace the battery. Alternatively, the battery 108 is integrated in the electrode pads 104 to decrease the number of replaceable AED components. In yet another embodiment, the battery 108 can be recharged using a docking station, i.e., without removing the battery from the AED or electrode pads. Since the AED device of the present invention is intended for a single use only, the battery 108 can be a low-capacity battery capable of delivering a limited number of shocks only, such as a maximum of 5 shocks at 150 Joules per shock, for example.

The alert module 110 comprises hardware and software for generating and relaying information, notification, and alerts to the user. The alert module 110 may generate device-generated visual alerts (e.g., LED, text, and display graphics), audible alerts (e.g., beeps from a buzzer, music, and voice prompts from a speaker), tactile alerts (e.g., vibration from a buzzer), or any combination thereof locally from the AED. The alert module 110 may also send messages to a device, remote system, facility, or individual, such as a nurse, hospital, ambulance, police, device manufacturer, and maintenance personnel, for example, via the wireless communication module 126. Preferably, only a limited number of alerts are generated to save power and prevent confounding the user, who is, for example, untrained in the use of an AED.

The user interface 112 comprises input means for receiving information from a user and output means for relaying information to the user. The user interface 112 preferably includes an LCD, touch screen, control buttons, switches, audio speakers, LED bulbs, vibrating elements, or any combination thereof. In a preferred embodiment, the user interface 112 comprises only a small number of components so that the AED 100 can be easily operated by an untrained individual and minimize the psychological stress arising from the AED's use. For example, the user interface 112 preferably comprises only a power button, a SHOCK button, and an INFORMATION button. The power button toggles the AED 100 between an ON or active state and an OFF or standby state. Preferably, before the power button is pressed to activate the AED 100 and during the AED standby state, the AED 100 displays either a "Ready for Use" alert or a "Not Ready for Use" alert. The SHOCK button provides the user the ability to generate a shock when "Shock Advised" event is determined by the AED processor 118. In other cases, pressing the SHOCK button does not generate a shock through the electrode pads 104. During a "Shock Advised" event, preferably a voice prompt and a graphical display inform the user that a shock is advised and that the SHOCK button needs to be pressed. Pressing the INFORMATION button on the user interface 112, on the other hand, generates AED information alerts, such as the number of shocks delivered and the condition of the patient as sensed by the sensor array 116. In another embodiment, the delivery of a shock is automatically performed by the AED 100 without user confirmation or intervention to further minimize user involvement. It is understood that any of the user input buttons, alone or in combination, may be used by the user to input a prompted deactivation command at the appropriate time.

The memory module 114 preferably comprises a criteria database 120 and the use state database 122. The criteria database 120 stores a plurality of criteria and thresholds for triggering a "Not Ready for Use" alert or deactivating the AED 100. The use state database 122 stores current information relating to various AED events, such as the duration of activation, the number of times the electrode pads have been deployed, the duration of an NSA event, and the number of shocks delivered.

The sensor array 116 comprises physiological sensors for monitoring the physiological state of a patient. The sensors include ECG sensors, oximetry sensors, and temperature sensors, among others. Preferably, the heart rhythm of the patient is monitored while the electrode pads 104 are mounted on the patient's body. When a shockable heart rhythm is detected, a "Shock Advised" condition is determined by the processor 118. Otherwise, an NSA condition results. Preferably, the sensor array 116 also comprises environmental sensors such as a temperature sensor, humidity sensor, vibration sensor, and GPS sensors, among others.

The wireless communication module 126 enables a two-way communication between the AED 100 and an external system, such as the central monitoring server 124, a desktop computer, 911 server, a medical personnel's cellphone, hospital network, manufacturer's network, and maintenance network, among others. In one embodiment of the present invention, the central monitoring server 124 monitors or controls a plurality of AEDs. When an AED is activated by a user, an activation message is preferably immediately sent to the central monitoring server 124 so that the central monitoring server 124 can monitor the AED's use state and respond accordingly. Alternatively, the activation message is sent during the deployment of the electrode pads 104. In response to the activation message, the central monitoring server 124 preferably immediately sends an emergency rescue team to the location of the AED. Preferably, each AED is registered to the central monitoring server 124 during the AED purchase to ensure that each AED can be monitored and maintained properly by the central monitoring server 124. Preferably, the activation message also comprises the emergency location, AED location information, device identification information, and owner identification, for example.

In another embodiment, the central monitoring server 124 transmits one or more control signals to the AED 100. The control signal may be used to establish a voice call between a medical professional and the user. The medical professional can then guide the user during the rescue operation. The control signal may also be an alert signal that can generate a visual, auditory, or tactile alert. The visual alert may comprise displaying the estimated time of arrival of an ambulance.

In a preferred embodiment, the central monitoring server 124 automatically provides software updates to the AED 100. Alternatively, this step may by manually performed by an authorized individual during a maintenance visit. The software updates may include updates to the operating system, drivers, programs, algorithms, graphics data, alert data, and communication protocols, for example. The criteria database 120 may also be updated via the central monitoring server 124. In another embodiment, the central monitoring server 124 monitors an expiration date of the AED 100. Preferably, when or shortly before the expiration date is reached, the central monitoring server preferably sends a notification to maintenance personnel to perform diagnostic and other maintenance tests on the AED and replace the electrode pads and battery.

Figure 2:
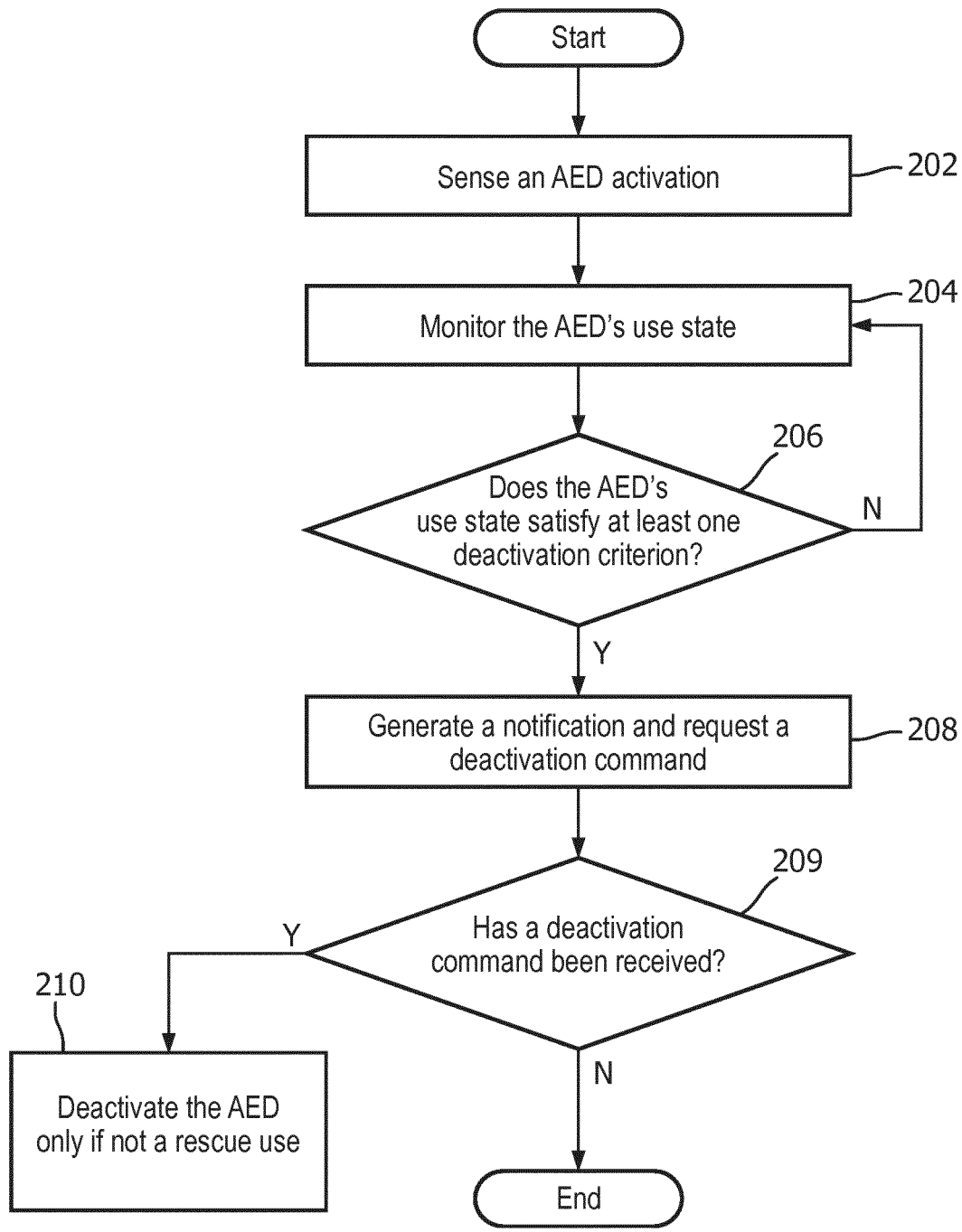
FIG. 2 illustrates a preferred method of limiting an activation of a single use AED.

FIG. 2 is a flowchart illustrating a preferred method of the present invention. When the AED is activated, the activation is sensed by the event monitoring module (step 202). The event monitoring module continuously monitors the AED's use state during the AED's active state (step 204). The AED's use state is then compared with a set of deactivation criteria to determine if a "Not Ready for Use" state is satisfied (step 206). If so, a notification is generated and a deactivation command is requested from the user to prevent the AED from being used until the replaceable parts have been replaced or maintained (step 208). If a user elects to send a deactivation command (step 209), the AED is deactivated (step 210).

It is very important that the AED not permit itself to be deactivated during a rescue event. Step 210 therefore should in a preferred embodiment only initiate deactivation if the AED is sensed as being handled in a non-rescue event manner, or to initiate deactivation only when the AED is in a stable standby condition, e.g. has been in standby for a number of hours after the last user-initiated activation. Sensing of a rescue use can be by sensing deployment of electrodes, charging of a high voltage circuit during activated use, sensed voice and ECG data, and the like.

Figure 3A:
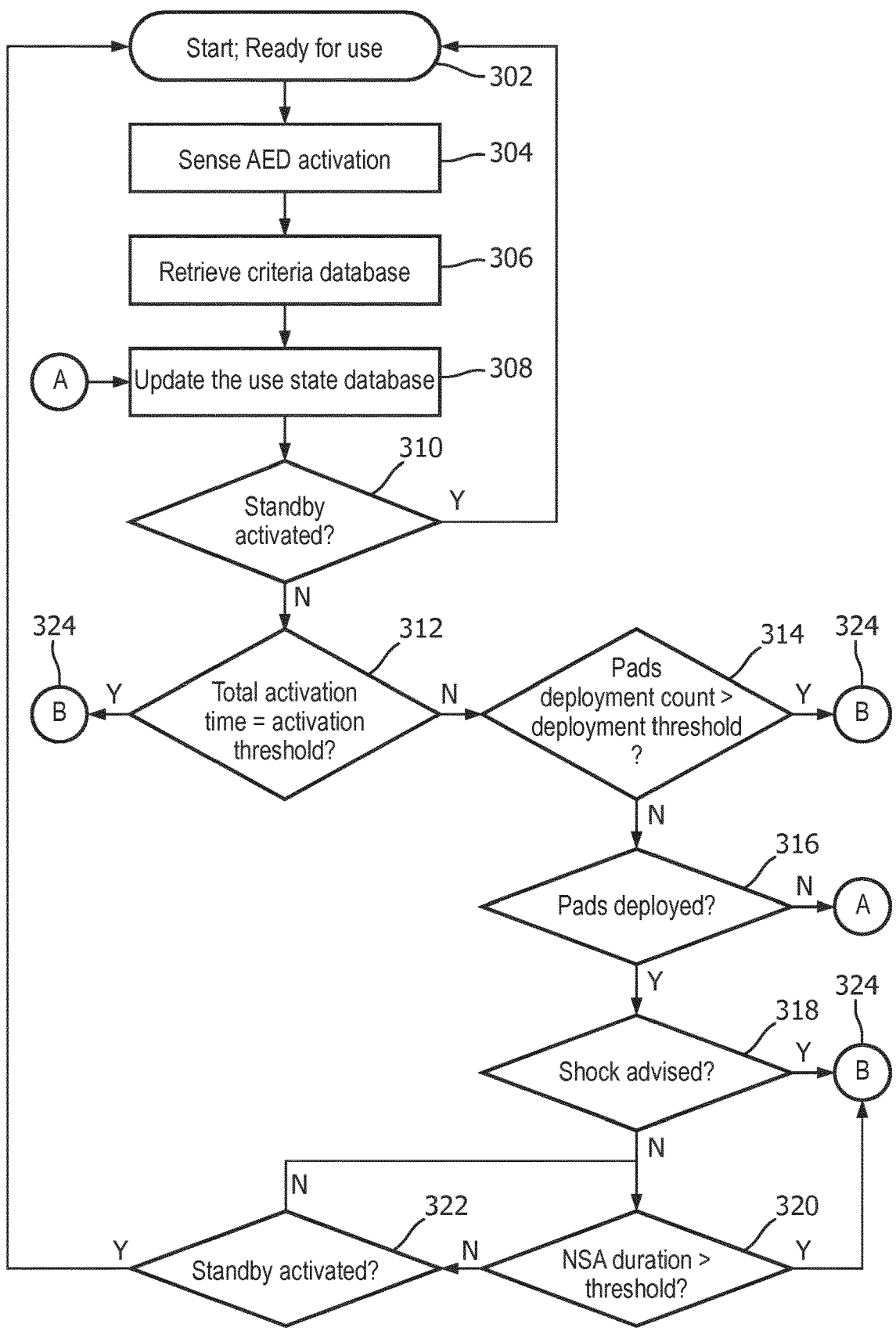
FIG. 3A is a flowchart illustrating a preferred method of how the AED is switched from a "Ready for Use" state to a "Not Ready for Use" state.
Figures 3B, 4:
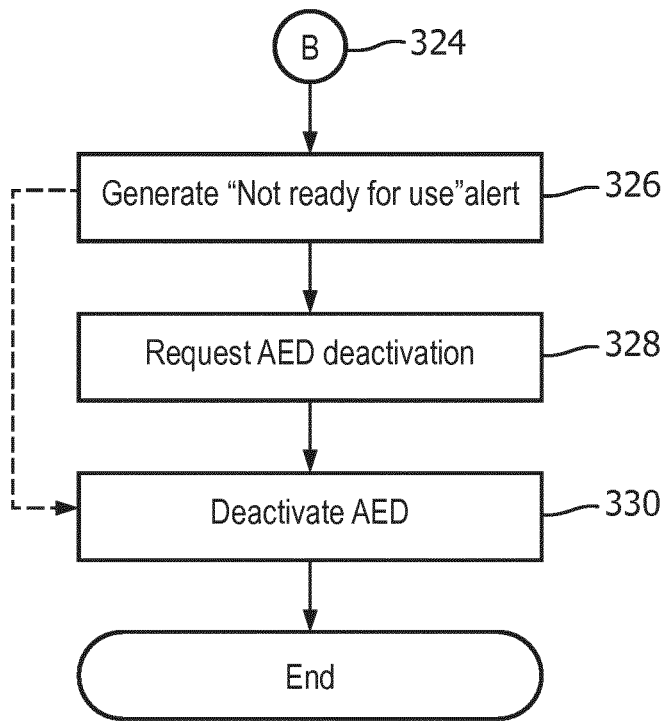
FIG. 3B illustrates a flowchart continued from FIG. 3A.
FIG. 4 is an example of a criteria database according to an embodiment of the present invention.

In one embodiment illustrated in FIGS. 3A and 3B, the event monitoring module monitors the duration of AED activation, the number of times the pads have been deployed, and the number of AED shock events. Before turning the AED on, the AED is preferably in a "Ready for Use" state (step 302). When the power button is pressed to activate the AED, the event monitoring module 102 senses the activation (step 302). The criteria database is retrieved (step 306) and the use state database is updated (step 308). Preferably, the user can switch the AED to a standby state (step 310), in which case the process loops back to step 302. If the standby state is not selected, the process then determines whether the total activation time exceeds the total activation time threshold in the criteria database (step 312) and whether the pads deployment count exceeds the pad deployment threshold in the criteria database (step 314). If both conditions are not satisfied, the process determines if the electrode pads have been deployed (step 316). If the electrode pads are not deployed, the operation loops back to step 308 to update the use state database. Otherwise, the process determines whether a shock has been advised (step 318). If an NSA is determined, the process proceeds to monitor the duration of the NSA. While the NSA duration remains below the NSA time threshold, the process continues monitoring the NSA duration until the standby state has been activated (step 322), after which the process returns to step 302. Alternatively, the process proceeds to step 324 if at least one of the conditions in steps 312, 314, 318, and 320 is satisfied. If at least one of the aforementioned conditions is satisfied, a "Not Ready for Use" alert is generated (step 326). The AED then asks the user if deactivation is desired (step 328). If the user elects to deactivate the AED, the AED is deactivated preferably until a maintenance operation (e.g., replacement of electrode pads and battery) is performed (step 330). Alternatively, the AED deactivation is performed without user confirmation (represented by the dotted lines in FIG. 3B).

FIG. 4 shows an example of the criteria database 120 according to an embodiment of the present invention. Shown in FIG. 4 are rows for "Total Activation Time" 402, "Pads Deployed Events" 404, "Pads Deployed NSA time" 406, and "Pads Deployed Shock Advised Events" 408. Also shown is an "Alert Threshold" column 410. For example, when the AED has been activated for 30 minutes since the last battery replacement, the AED may be switched to a "Not Ready for Use" state. A "Pads Deployed Events" threshold of 3, for example, allows the electrode pads to be deployed for a maximum of 3 times. When the electrode pads have been deployed, and an NSA event is determined, the duration of the NSA event is monitored. An NSA duration of 15 minutes, for example, will preferably switch the AED to a "Not Ready for Use" state. A "Shock Advised" threshold of 1, for example, only allows a single shock delivery, after which the AED is switched to a "Not Ready for Use" state. In one embodiment of the present invention, data in the criteria database 120 is provided and updated by a medical practitioner, medical institution, hospital, manufacturer, maintenance personnel, or the central monitoring server 124.

Figures 5, 6:
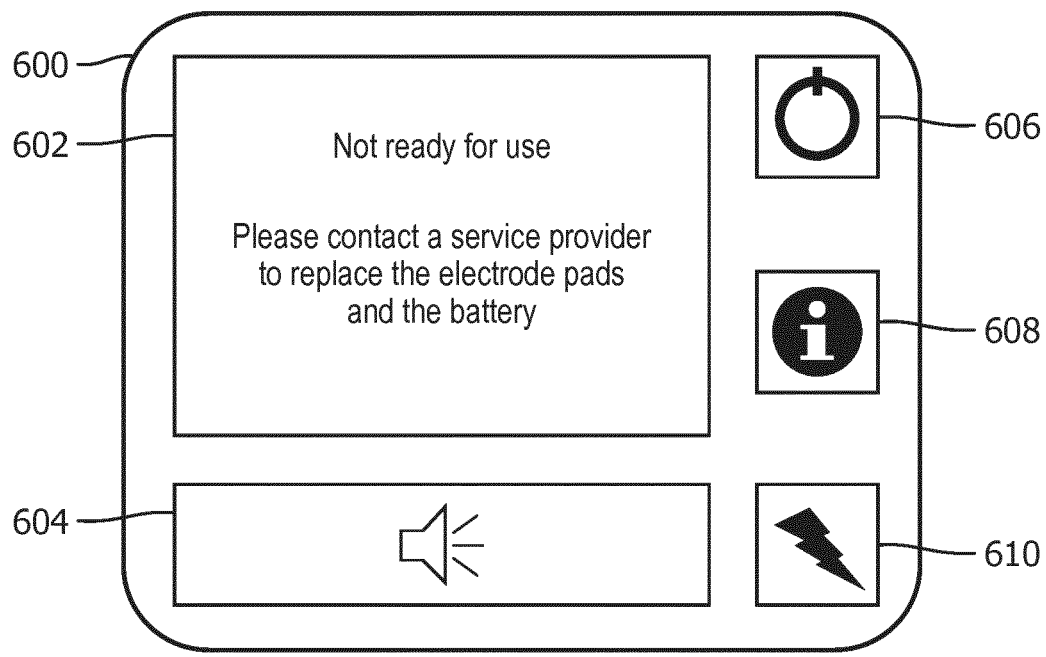
FIG. 5 is an example a of use state database according to an embodiment of the present invention.
FIG. 6 is an embodiment of an AED user interface according to an embodiment of the present invention.

FIG. 5 shows an example of a use state database 122 according to an embodiment of the present invention. Shown in FIG. 5 are real-time data of the AED's use state, comprising a "Total Activation Time" 502, "Pads Deployed Events" 504, "Pads Deployed NSA time" 506, and "Pads Deployed Shock Advised Events" 508. The values under column 510 are compared with threshold values in the criteria database 120 to determine whether the AED needs to be switched from a "Ready for Use" state to a "Not Ready for Use" state.

FIG. 6 shows an embodiment of a user interface 600, which comprises a display 602, speaker 604, power button 606, information button 608, and shock button 610. The small number of user interface components provide simplicity and user-friendliness to the AED and minimizes confounding an untrained individual during an emergency rescue operation. Additionally, the small number of user interface components also minimizes the total cost of the AED. In another embodiment, the AED does not comprise a shock button to further minimize user involvement. When a "Shock Advised" event is detected, the AED preferably automatically delivers a shock.

Figure 7:
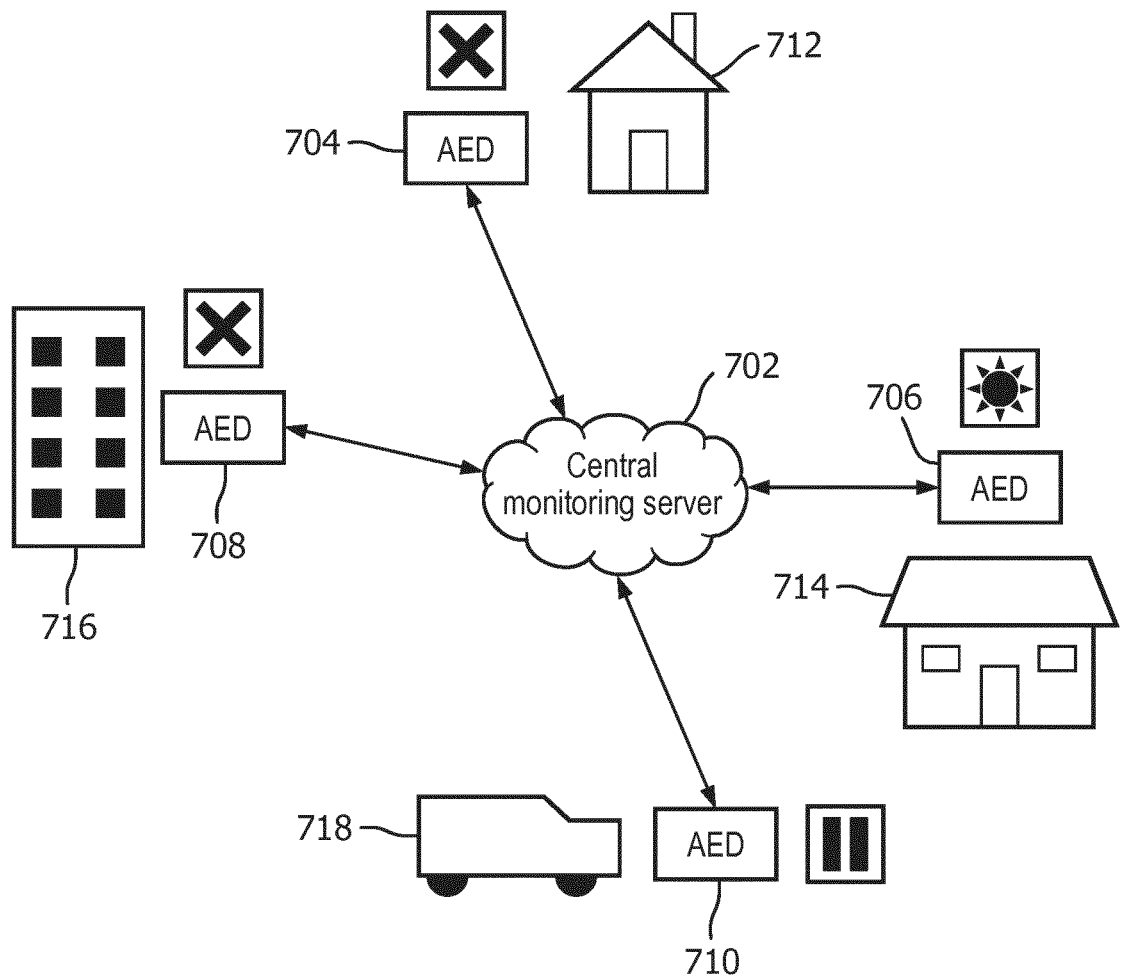
FIG. 7 illustrates a network of AEDs monitored by a central monitoring server according to an embodiment of the present invention.

In another embodiment of the present invention illustrated in FIG. 7, a plurality of AEDs in different locations are connected, controlled, or monitored by the central monitoring server 702. The plurality of AEDs 704, 706, 708, and 710 are stationed in residence 712, residence 714, office building 716, and private vehicle 718, respectively. The use state of the AED 704, 706, 708, and 710 are preferably periodically or a-periodically transmitted to the central monitoring server 702. The status of AED 704 and 708 are represented by an "X" symbol indicating the need to repair the AED or replace the AED disposable accessories. The status of AED 706 is represented by a "sun" symbol indicating that AED 706 is currently active and in use. The status of AED 710 is represented by a "pause" symbol, indicating that AED 710 is on standby.

In one embodiment of the present invention, a male patient suffering from arrhythmia passes out inside his residence. The patient's daughter finds the patient on the floor and immediately deploys a single use AED. She follows the instructions provided by the AED's voice prompt. She positions the electrodes on the patient's right chest and lower left rib cage as instructed by the AED. During initialization, the AED displays a "Ready for Use" text on the AED display to indicate that the AED can be used for the present emergency. An event monitoring module inside the AED checks the total activation time, the number of times the pads have been deployed, and the total number of charges delivered. The event monitoring module determines that the total activation time is 15 minutes, which is the accumulated sum from previous AED activation times. The event monitoring module also determines that the pads have been deployed only 1 time in a previous session and that no shocks have been delivered yet with the AED's present battery. The AED then analyzes the heart rhythm and determines that no shock should be advised. The daughter then removes the electrode pads, re-stows the electrode pads on the AED's electrode cartridge, and the AED is returned to a standby mode.

One week after the said event, the male patient suffers another arrhythmia and the daughter deploys the same AED. This time the event monitoring module determines that the total activation time has reached 28 minutes, the pads have been deployed 2 times, and no shocks have been delivered yet using the AED's present battery. The AED advises a shock, and a shock is delivered to the patient. Simultaneously, the AED contacts a 911 center to request an emergency rescue team. The AED is deactivated after the delivery of the single shock, and a "Not Ready for Use" alert is then generated. Upon arrival, the emergency rescue team proceeds with the rescue operation. After the emergency event, the electrode pads are removed by the daughter by disconnecting the electrode from the electrode port on the AED. The battery is also removed from the AED and replaced with a new battery.

In another embodiment of the present invention, when the AED is switched to a "Not Ready for Use" state, the AED immediately relays the AED's use state to the central monitoring server. The central monitoring server then schedules a service operation so that an AED technician can perform a maintenance check on the AED and replace the electrode pads and the battery.

The present invention is not intended to be restricted to the several embodiments of the invention described above. Other variations that may be envisioned by those skilled in the art are intended to fall within the disclosure.

What is claimed is:

1. A single use automated external defibrillator (AED) device, comprising:
   a battery;
   a pair of electrode pads;
   a wireless communication module for communicating with a central monitoring server;
   a hardware memory module comprising a use state database and a criteria database;
   an event monitoring module in communication with the hardware memory module and configured to monitor an AED use state during an activation period; and
   an alert module in communication with the event monitoring module, configured to issue an alert that the AED is not ready for use based upon one of a total activation time as compared to a total activation time alert threshold and a pads deployed time with a no-shock-advised (NSA) condition as sensed from the pair of electrode pads as compared to a pads deployed NSA time alert threshold.

2. The AED device of claim 1, further comprising at least one external port for removably coupling the pair of electrode pads to the AED.

3. The AED device of claim 1,
   wherein the alert module is further configured to issue an alert based upon a sensed number of times that the pair of electrode pads have been deployed as compared to a pads deployed event alert threshold criteria that is stored in the criteria database, and
   further wherein the pads deployed event alert threshold criteria is two or more.

4. The AED device of claim 1, wherein the battery is sized to deliver no more than five shocks of 150 Joules per shock.

5. The AED device of claim 1, further comprising a user interface in communication with the alert module, the user interface configured to generate a notification request to deactivate the AED and to receive a deactivation command.

6. The AED device of claim 5, further comprising a processor in communication with the user interface, the processor configured to deactivate the AED responsive to the received deactivation command.

7. The AED device of claim 1, wherein the wireless communication module is in communication with the alert module, the wireless communication module configured to transmit the AED use state to a central monitoring server.

\* \* \* \* \*